United States Patent [19]

Richmond

[11] 4,292,027
[45] Sep. 29, 1981

[54] SEALING DENTAL COLLET

[75] Inventor: George E. Richmond, Ladue, Mo.

[73] Assignee: Young Dental Manufacturing Co., Hazelwood, Mo.

[21] Appl. No.: 59,525

[22] Filed: Jul. 23, 1979

[51] Int. Cl.³ .............................................. A61C 1/14
[52] U.S. Cl. .................................. 433/127; 433/115; 279/1 Q
[58] Field of Search .............. 433/127, 115, 116, 126, 433/133; 279/1 Q, 1 R

[56] References Cited

U.S. PATENT DOCUMENTS

| | | | |
|---|---|---|---|
| 1,678,097 | 7/1928 | Andresen | 433/115 |
| 1,837,938 | 12/1931 | Young | 433/166 |
| 2,005,849 | 6/1935 | Skinner | 433/133 |
| 2,469,261 | 5/1949 | Cooper | 433/112 |
| 3,098,299 | 7/1963 | Page | 433/115 |
| 3,293,402 | 12/1966 | Graham | 279/1 Q |
| 3,426,429 | 2/1969 | Hoffmeister et al. | 433/127 |
| 3,542,372 | 11/1970 | Edwardson | 433/116 |

FOREIGN PATENT DOCUMENTS

| | | | |
|---|---|---|---|
| 226359 | 8/1962 | Fed. Rep. of Germany | 433/126 |
| 355653 | 4/1973 | Sweden | 433/115 |

Primary Examiner—Gene Mancene
Assistant Examiner—John J. Wilson
Attorney, Agent, or Firm—Rogers, Eilers & Howell

[57] ABSTRACT

A collet of somewhat flexible plastic for holding a dental tool in a dental handpiece, has an inner body which fits within a socket in the burr tube of the handpiece, and at its outer end extends outwardly into a hub and then rearwardly into a cylindrical skirt which fits between the outer surface of the bearing for the burr tube and the inner surface of a counterbore in the handpiece. Centrifugal force caused by rotation of the burr tube flares the skirt outwardly against the counterbore surface to provide a seal therebetween. In a modification the skirt slants outwardly to contact the counterbore surface when the skirt is stationary. A modified skirt tapers from its connection to the hub to the skirt end.

In another modification, the collet has a bore in its inner end, with the handpiece end cap, the driven gear and the burr tube having bores aligned with the collet bore so that a burr extractor pin can extend through the bores to push the dental tool out of the collet. The extractor pin in one form has a flat head, and in another form has a looped end for insertion of a finger.

11 Claims, 7 Drawing Figures

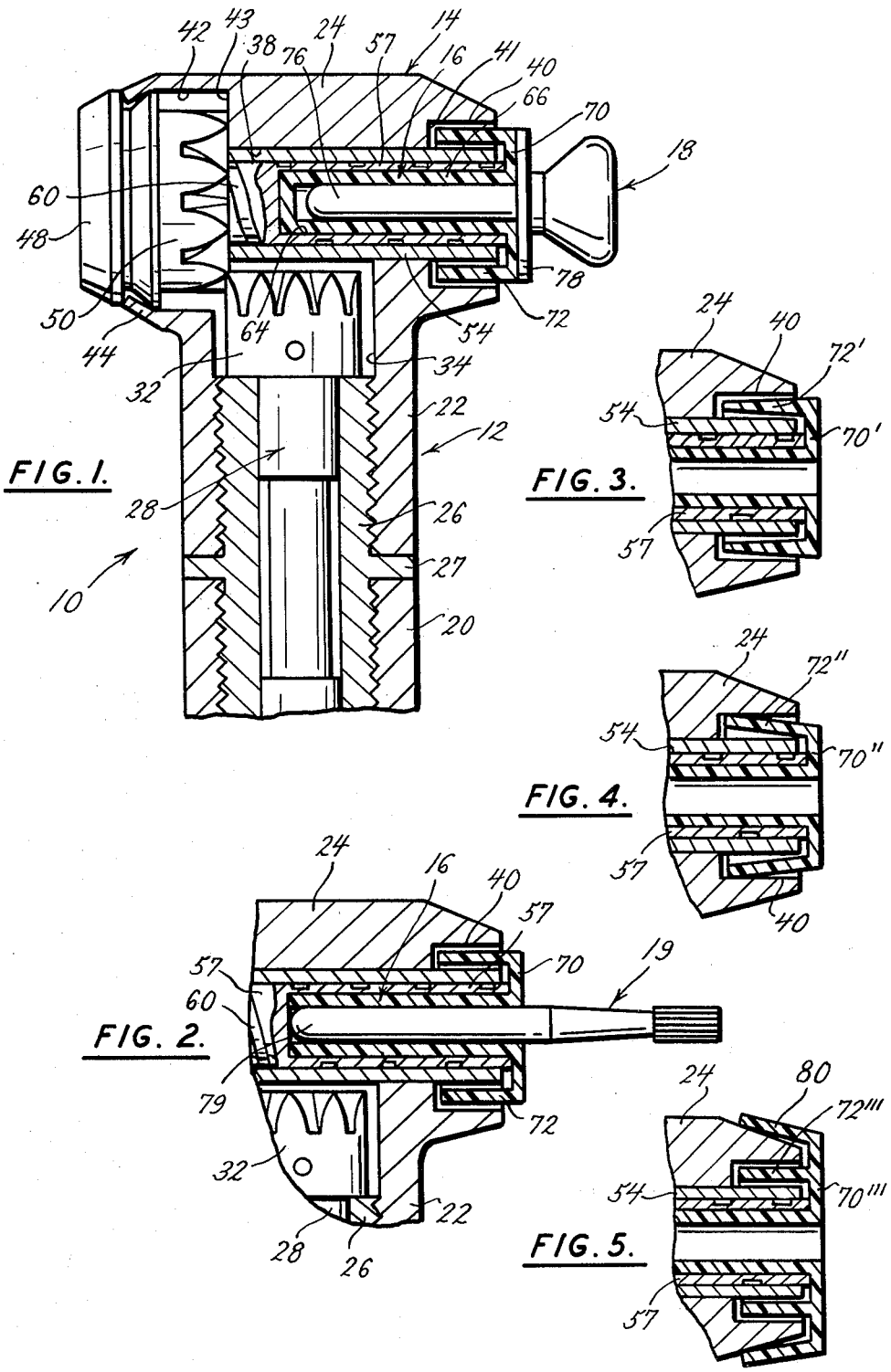

SEALING DENTAL COLLET

BACKGROUND AND FIELD OF THE INVENTION

The present invention is concerned with dental hand pieces, it being an object to provide a collet arrangement fitting in a dental burr tube with means affected by centrifugal force to seal off workable parts of the handpiece from substances which the handpiece comes into contact with, such as abrasives, ground tooth matter, particulate food matter, saliva and bacteria. In the prior art, problems have existed with such matter entering dental handpieces and causing wear and tear, corrosion, and the breeding of bacteria within handpieces. Working parts within handpieces are especially affected when such debris contacts them.

A specific object is an engaging member for a dental tool having a flexible flange or skirt means engageable in a counterbore of a handpiece head wherein it may seal by centrifugal force, and which is independent from the tool.

A further object is to provide an engaging member for a dental tool with such a flexible flange seal that does not subject the sealing means to thrust forces in use.

In the prior art, devices used to block pumice such as that shown in U.S. Pat. No. 3,407,502 to G. E. Richmond there is an annular bead 79 on a cap 60 which fits into a groove 78 in a hub 68 for the purpose of blocking pumice. However these parts being of metal do not provide a centrifugal force seal.

Other dental handpieces are shown in Richmond U.S. Pat. Nos. 3,436,830, Bailey 4,014,099, and Fernald 1,170,523 and Etherington 3,978,586 and the art cited in them. Cooper 2,469,261 purports to illustrate an arrangement by which a rubber cup can seal by compression, but it is noted that, among other things, the driving mechanism between the shaft and the rubber cup is part of the same mechanism that is supposed to give the sealing arrangement. Another part of the Cooper sealing arrangement is part of the dental tool used.

The present invention improves over the prior art. The collet is of plastic and molded in one piece. The skirt of the collet is resilient, and the remainder of the collet can also be resilient or can be of metal. The sealing means, that is the skirt, is a part of the collet and is not attached to the dental tool such as a dental burr. This means that a single skirted collet can be used with several different tools of the same or different type. Having one skirt on the collet thus is much more economical than having a sealing means provided for each tool.

The collet, being molded of one piece, can be readily replaced for repairs by another such collet. The collet preferably has a body with a closed end which prevents passage of debris through the collet into the burr tube and towards the working parts of the handpiece. With the present device, it is unnecessary to use a screw to hold the tool in the collet because of the collet friction grip.

In a modification, the skirt tapers from its hub connection to narrower width at the skirt end, which allows greater movement of the skirt end by centrifugal force.

Another modification has an outwardly slanting skirt that contacts the surface of the counterbore when the skirt is stationary.

In another modification an extractor pin is provided for removal of a dental tool from a collet in a modified head. The interior end of the collet has a pin receiving bore, and the modified head has bores through its cap, driven gear and burr tube that are aligned with the collet pin bore for receipt of the pin shaft so that the pin can push the dental tool out of the collet. One form of the pin has a flat head with a neck to space the head away from the handpiece cap to provide for insertion of a fingernail or other thin object to pry the pin. Another form of the extractor pin has a looped end for insertion of a finger to push and pull on the pin shaft.

DESCRIPTION OF THE DRAWINGS

FIG. 1 is a diametrical section view of the head end of a dental handpiece showing the invention with a standard knob for receiving a dental cup.

FIG. 2 is a diametrical section of the end of the head of the dental handpiece, with a dental burr shown inserted within the collet.

FIG. 3 is a diametrical section of the end of the dental handpiece, showing a modification of the invention with a tapered skirt.

FIG. 4 is a diametrical section of the end of the dental handpiece showing another modification of the invention having an outwardly slanting skirt.

FIG. 5 is a diametrical section of the handpiece end, showing a double skirted modification.

DESCRIPTION OF THE PREFERRED EMBODIMENT

Figure 6:
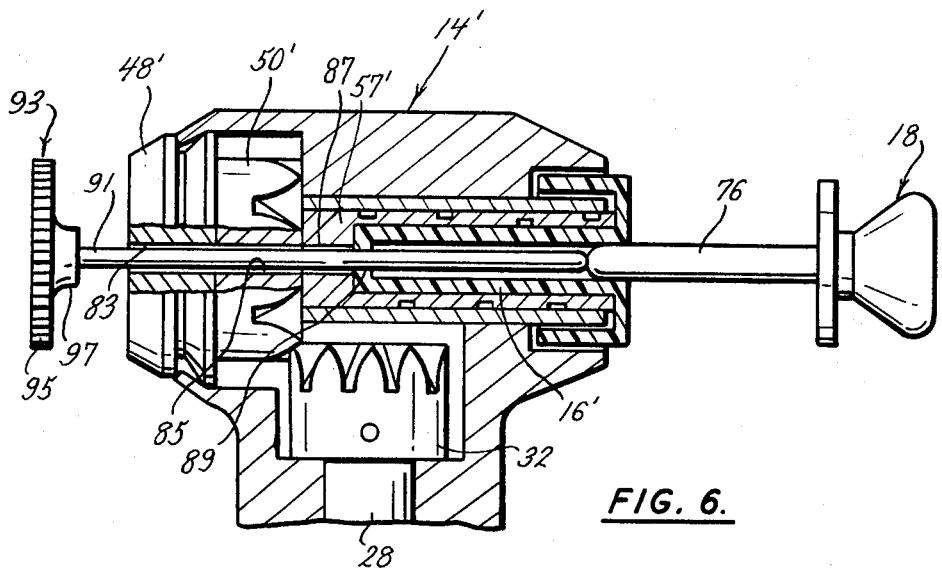
FIG. 6 is a diametrical section of the head of a handpiece showing a pin for extracting the dental tool, and bores in the cap, gear, burr tube and collet for receipt of the pin.

The dental handpiece 10 as seen in FIG. 1 is more particularly described in application Ser. No. 953,473 filed Oct. 23, 1978. It generally comprises a sleeve assembly 12 that is part of the handle of the handpieces, a head assembly 14, and a novel sealing plastic skirted friction collet 16 which has inserted within its socket the shaft of a dental tool 18. FIG. 2 shows a dental burr 19 inserted within the collet 16.

More specifically, the sleeve assembly 12 comprises an outer sleeve 20 and a sleeve 22 which extends transversely into the head 24 of the head assembly. A tubular double ended threaded drive shaft bearing 26 having an intermediate circular flange 27 has its exterior threads within interior threads of sleeves 20 and 22, with the abutting sleeve ends flush against the walls of flange 27. Bearing 26 has a central bore which receives a solid drive shaft 28 driven by an electric or air motor (not shown), and having its outer end drivingly engaged to a drive gear 32 having a flat inner end flush with the outer end of bearing 26. Gear 32 is housed within a bore 34 with the diameter of bore 34 and the threaded bore of sleeve 22 being sufficient to allow the gear 32 to pass through them for removal.

The head assembly 14 comprises the head 24 aforesaid which has a cylindrical bore 38 extending transversely to and in connection with the bore 34. The bore 38 extends rightwardly (in the drawings) into a recess such as an enlarged cylindrical counterbore 40 having a flat end surface 41; and leftwardly into a larger cylindrical counterbore 42, having a flat shoulder surface 43 and an end wall 44 swedged to extend into a peripheral groove of an end cap 48 which has a flat right or inner side. The swedged wall seals the cap firmly to the head, and prevents ingress of debris.

A metal bearing 54 having a cylindrical outer surface and cylindrical bore is press fitted within bore 38, and extends rightwardly out into the enlarged counterbore 40. The bearing extension into counterbore 40 forms an annular recess between the cylinder surface of counterbore 40 and the outer surface of the projecting bearing 54.

A driven shaft or burr tube 57 has its outer cylindrical surface rotatably fitted closely within the cylindrical bore of bearing 54. The burr tube right end projects into the counterbore 40, slightly beyond the projecting end of the bearing 54. The burr tube 57 may have on its outer surface spiral grooves 60 that open in and beyond the counterbore 40. Burr tube 57 has a cylindrical socket 64, extending axially from its open end, the socket 44 having a flat closed end. The left end of the tube 57 is secured to a driven gear 50 to be driven thereby.

The driven gear 50 is housed within enlarged left end bore 42 so that its beveled teeth are in mesh with the teeth of drive gear 32. The teeth of gear 50 abut the flat shoulder surface 43. The left side of gear 50 is flush against the right end of cap 48 to provide a thrust bearing for the gear.

The collet 16, which can be molded in one piece of plastic such as sold under the trademark Teflon, or of nylon, has a cylindrical body portion 66 press fitted within burr tube socket 64 to be driven therewith, the flat left end of body 66 preferably engaging against the socket flat end. Preferably the left end of the collet is closed to increase the sealing effect thereof. The right open end of collet 16 extends outwardly perpendicularly to body 66 into a hub 70 having a flat annular outer surface. The outer rim of hub 70 has a cylindrical skirt 72 which extends leftwardly into counterbore 40 to be normally slightly distanced from the surface of counterbore 40. When the burr tube is rotated, centrifugal force flares the somewhat flexible skirt 72 outwardly so that the skirt bears sealingly against the counterbore cylindrical surface.

For example, the cylindrical body 66 can have an outside diameter of about 0.090 in. (0.229 cm). Skirt 72 can have an outer diameter of about 3/16 in. (0.476 cm), a uniform thickness of approximately 0.016 in. (0.041 cm) and can be typically about 3/32 in (0.238 cm) long axially. The distance between the skirt outer surface and the cylindrical surface of bore 40 is approximately 0.005 in. (0.013 cm) and preferably not greater than 0.008 in. (0.0203 cm). With cylindrical Teflon or nylon, such dimensions allow the skirt to seal at rotational speeds of from about 1600 to 2000 rpms and upward.

The body 66 can if desired be of heat treated metal with spring tension and slotted to provide gripping jaws. The hub 70 can be of the same metal with the plastic skirt crimped or otherwise secured to the hub to be held thereto, as by molding the plastic skirt into the hub or onto the body 66, to be retained thereon against rotation relative thereto.

The skirt 72 can be of such length, if desired, to have its left end contact the flat surface 41 of counterbore 40 to provide a stationary seal at the skirt end. However, such contact could cause friction heat at the flat surface 41 during movement, which is undesirable. The length of the bearing 54 and burr tube 57 are preferably sufficient to position the skirt end from such contact with the flat surface 41.

The dental tool 18, depicted in FIG. 1, is a typical one upon which different dental tools such as a cleaning cup, may be snapped. Tool 18 has a cylindrical shaft 76 which is snugly received within the bore of collet body 66 to provide rotary drive from the burr tube through the collet to the tool. (These parts may be non-cylindrical, to cause the drive.) The left flat surface of circular flange 78 of tool 18 fits flush against the flat face of hub 70. In the case of FIG. 1, the shaft 76 does not extend to the end of the body 66 bore, and the bore is closed at that end. In the case of FIG. 2, however, the end of shaft 79 of burr 19 extends to the end of the collet body 66 to rest against the flat end of the body bore. The former on FIG. 1 construction is preferred as it provides a further seal against ingress foreign matter.

The long bearing 54 supporting the collet affords an extended single bearing surface that can be made to extremely close tolerances. This affords steady support for the collet to position it beyond the face of bore 40 as well as a long and restrictive path resisting passage of foreign matter from the open to the closed end of the head. It also minimizes eccentricities and irregularities that can cause uneven rotation at the high speeds encountered in this type of equipment. Heretofore one relatively short bearing, or two bearings have been used. If two, one is usually near the open end of the head and the other near the other end. Two bearings have the difficulty of maintaining the two in appropriate close alignment, absent which abnormal wear quickly destroys the head.

The rotation of the burr tube is in a direction so that the spiral 60 affords screwlike drive of the debris which may enter past the skirt to force the debris to the right away from driven gear 50.

OPERATION

In operation, the user presses the shaft of the dental tool such as one shaft 76 of the tool 18, or the shaft 79 of the burr 19, into the bore of collet body 66. The shaft is sized to be received snugly so that the plastic collet walls hold it against slippage when the burr tube is rotated. However, the grip of the collet body about the shaft is such that the tool shaft can be withdrawn from the collet by a linear pull of the hand.

When the collet rotates the collet skirt 72, the skirt being made of flexible plastic, flares out as a result of centrifugal force so that it presses against the walls of the cylindrical bore 40. This contact between the skirt and the walls of counterbore 40 blocks the passageway therebetween for abrasive materials, particulate food matter, tooth grindings, bacteria, saliva, and other matter so that such material cannot work its way back to the driven gear 50 through the interface between bore 38 and bearing 54, or between the bearing 54 interior surface and the burr tube. The axial length of the skirt promotes a good centrifugal seal. The skirt 72 may be sufficiently close to the walls of counterbore 40 so that at rest it acts to some extent to block matter from passing between it and the walls of counterbore 40.

Since the tool shaft fits into a socket that is preferably closed at its end, ingress about the surface of the shaft towards the driven gear is blocked. As a result of preventing offensive material from reaching the driven gear 50, the driving gear 32 is also protected as are the other working surfaces.

As the dental tool 18 rotates (and as the burr tool of FIG. 2 rotates) thrust forces applied to the tool are transferred through the burr tube to the end gear 50 and thence against the flat inner surface of cap 48 so that the cap acts as a thrust bearing against these forces.

FIG. 3 shows a modification. The modified skirt 72', as seen FIG. 3, tapers from a thickness of about 0.025 inches (0.064 cm) at its connections to the hub 70', to a thickness of about 0.005 in (0.013 cm) at the end of the skirt. The collet is otherwise of the same structure discussed for FIG. 1 or FIG. 2.

When the tapered skirt 72' is rotated it too flares out to contact the cylindrical surface of counterbore 40. The tapering of the skirt reduces rigidity at the skirt end so that the smaller end can flare out to touch the counterbore surface at lower rotational speeds than required for an untapered skirt with a thickness of 0.025 in. (0.064 cm). The larger end of the skirt 72' near the hub allows for greater material to be used to connect the skirt to the hub, which strengthens that connection.

FIG. 4 shows another modification in which a skirt 72" slants outwardly from its connection to the hub 70" so that the end of the skirt 72" contacts the cylindrical surface of counterbore 40 when the skirt 72' is stationary. The stationary seal of the skirt 72" blocks the passageway between the counterbore surface and the skirt when the instrument is static, to further resist passage of debris to the bearing, burr tube and gear areas. The hub 70" and collet body are the same as discussed for FIG. 1 and the collet body though preferably closed as shown in FIG. 1, can also be open as shown for FIG. 2.

Upon rotation of the skirt 72", the skirt end moves outwardly to contact the wall with greater force so as to affect a greater seal than is provided when the skirt 72" is stationary. The skirt 72" can have the same tapering as shown in FIG. 3 with the skirt having a length to allow the tapered narrower end of the skirt to contact the cylindrical surface of counterbore 40 when the skirt is stationary.

FIG. 5 shows another modification featuring a double skirted arrangement. The collet hub 70''' has a first inner skirt 72''' which has the same dimensions set forth for skirt 72 and which extends leftwardly into counterbore 40 in the same fashion as described for FIGS. 1 and 2. The hub 70''' extends outwardly beyond inner skirt 72''', and at its outer end has an integral outer skirt 80 which is also composed of flexible plastic and can have a thickness of approximately 0.016 in. to 0.032 (0.041 cm to 0.082 cm). The skirt 80 is tapered to a lesser degree than the taper for the outer surface of head 24, so that the inner tip of the skirt, rather than the entire interior skirt surface, bears on the outer tapered surface of the head 24 to provide a seal. The collet body 66 can be otherwise the same as the preferably closed ended type of FIG. 1, or can be the open ended type of FIG. 2. When the collet is stationary relative to the head, outer skirt 80, by sealing against the outer head surface, forms a static seal about counterbore 40 to prevent passage of debris into counterbore 40, and into the bearings and gears. Upon rotation, the inner skirt 72''' moves outwardly under centrifugal force to provide a seal against the inner surface of counterbore 40, as described for FIGS. 1 and 2, while the outer skirt 80 may have its seal broken due to centrifugal force. Because outer skirt 80 is only approximately 3/32 in. (0.238 cm) long, its outward movement is limited. Since the outer skirt 80, under static conditions, only has its tip in contact with the surface of head 24, upon rotation friction between skirt 80 and head 24 is not as great as it would be if the inner surface of skirt 80 were flush with the surface of head 24 under static conditions.

It can be understood that the collet hub is provided in all the embodiments shown to project the skirt outwardly from the burr tube so it can extend around the bearing 54. In the absence of bearing 54, the skirt could slant from the outer end of collet body 66 to be positioned close enough to the counterbore cylindrical surface so that a seal against the surface results from centrifugal force when the skirt is rotated; or the skirt can slant so as to contact the cylindrical counterbore 40 surface to provide a seal when the skirt is stationary, with the skirt moving out with greater force during rotation.

FIG. 6 is another modification for providing a means to extract the burr tool 18 from the collet, showing a head assembly 14' having a cap 48' with a center cylindrical bore 83, a gear 50' with a center cylindrical bore 85, a burr tube 57' having a center cylindrical bore 87, and a collet 16' having a center cylindrical bore 89 extending through its inner end. The bores 83, 85, 87 and 89 are concentrically aligned so as to receive the elongated cylindrical shaft 91 of a burr extractor pin 93. The bores 83, 85 and 87 are of a diameter slightly greater than the diameter of shaft 91, while the bore 89 is sized so that shaft 91 fits snugly within it.

In the preferred embodiment, the pin shaft diameter is approximately one half of the diameter of the tool shaft 76, as shown in FIG. 6. Other than for the existence of the bores 83, 85, 87 and 89, the cap 48', gear 50', burr tube 57', and collet 16' respectively are identical to their corresponding parts of FIG. 1.

The pin 93 has a head 95 with a smaller tapered neck 97 extending into shaft 91. The smaller end of neck 97 is of a diameter greater than that of bore 83 so that when the pin shaft is inserted, as shown in FIG. 6, to push the tool 18 out of the collet 16', pin head 95 will be spaced from the flat end of cap 48' by a distance at least as great as that of the thickness of the neck 97. This permits the insertion of a fingernail or other thin object beneath the head 95 to pry it away from cap 48'.

Thus, after the tool 18 has been used, the shaft 91 of pin 93 can be inserted through the bores 83, 85, 87 and 89 to push the inner end of tool 18 with a force sufficient to overcome the drive grip of the collet 16' about the tool shaft 76. The length of pin shaft 91 is shown to be such that when the end of neck 97 is flush against cap 48', the end of shaft 91 extends slightly beyond the outer edge of the hub of collet 16'. After tool 18 is removed, the head 95 can be grasped by the fingers to pull the pin 93 out of the head assembly 14 so that another tool can be inserted with the collet 16'. If desired a plastic plug can be provided to be inserted from the outside of the cap 48' into the cap bore 83 to seal bore 83 after the pin 93 has been used.

The tool 18 of FIG. 1 can be removed from collet 16 of FIG. 1 by use of a small wrench; or by a firm grasp and pull by the fingers. However, the extractor pin 93 provides ease in the removal of the tool 18.

The same arrangement as shown in FIG. 6 can be provided for the structure of FIG. 2, with the only difference being that the FIG. 2 collet has no rear end wall and the extractor pin bore extending through burr tube 57 would be of a size to snugly receive the pin shaft 91 and would extend through the burr tube to push the tool 19, or any other type of tool, from the collet.

Figure 7:
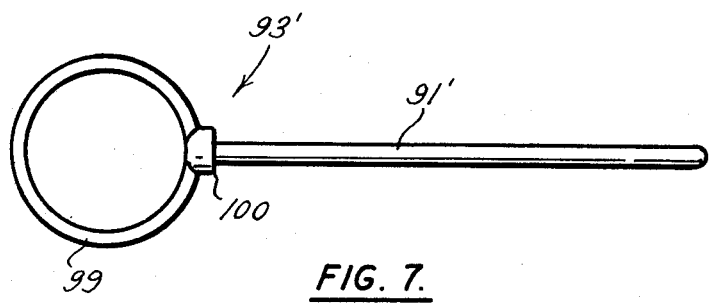
FIG. 7 shows a modified burr extractor pin having a loop for receiving a finger.

FIG. 7 shows another type of extractor pin 93' having a shaft 91' of the same length and diameter as shank 91, but having a finger sized loop 99 at the outer end. The enlarged neck 100 of the loop adjacent the end of shank 91 is of slightly larger diameter than the bore 83 of cap 48'. The pin 93 may be easily operated by insertion of a finger through the loop 99 to push the pin shaft 91 into the head assembly to remove the dental tool shank from the assembly. The pin 93' is then easily removed from the head assembly by pulling upon loop 99.

The invention thus provides the advantage of having a sealing means, that is, the skirt, on the handpiece rather than on the tool that is inserted in the collet. The skirt, being a part of the collet remains with the head after the tool has been withdrawn from the head. One collet can thus be used for several tools of the same type or different type and it is unnecessary to provide a skirt for each tool inserted in the handpiece. This is more economical than having a skirt for every tool. Likewise the double skirted collet can be used for several tools of the same or different type, since both skirts are part of the collet.

The collet, being molded of one piece, can be readily replaced for repairs by another such collet. The closed collet socket end of FIG. 1 (at the left of the collet) block grit and the aforesaid debris from passing through the collet into the burr tube and towards the working parts of the handpiece. The extractor pin modification can be used to facilitate removal of the tool, especially in cases where the collet is designed to have a very strong grip. With the skirted collet, it is unnecessary to use a screw to hold the tool in the collet because of the friction grip of the collet.

What is claimed is:

1. A dental handpiece assembly for rotating a dental tool comprising:
   (a) a head for receiving the tool, the head having a recess at the end of the head from which the tool extends, said recess has a side surface; and
   (b) a tool engaging member rotatable received within the head for engaging the tool for rotational drive relative to the head; and
   (c) a flexible skirt extending outwardly from connection with the tool engaging member and having its end within said head recess so that rotation of the skirt moves the skirt outwardly by centrifugal force to engage the surface of the recess to form a seal between the recess and the skirt.

2. The structure of claim 1 further comprising a hub projecting outwardly from the extension member, and wherein the skirt is of cylindrical shape and is connected to the hub to extend rearwardly therefrom.

3. The structure of claim 1 further comprising a burr tube rotatably mounted to the head, said tool engaging member mounted to said burr tube to be driven thereby, said burr tube projecting into said recess a sufficient distance to position the skirt for engaging the recesss surface when the skirt moves outwardly under centrifugal force.

4. The structure of claim 3 further comprising a bearing, said burr tube mounted within said bearing for rotation therein, said bearing extending within the recess to assist in positioning the skirt for centrifugal force sealing.

5. The structure of claim 1 wherein the flexible skirt is slanted outwardly from the tool engaging member so that the end of the skirt is in contact with the side surface of the recess when the tool engaging member is stationary relative to the head.

6. The structure of claim 1 wherein the skirt tapers from a larger thickness at its connection with the tooling engagement member to a narrower thickness towards the end of the skirt.

7. The structure of claim 1 further comprising: an outer surface for the head, and a second outer flexible skirt projecting beyond the said head recess and engaging the outer surface of the head to form a seal between said head outer surface and said second skirt when said tool engaging member is stationary relative to the head.

8. The structure of claim 1 further comprising:
   (a) said tool engaging member having a rear opening; and
   (b) an extractor pin having a shaft sized to pass through the rear opening of the tool engaging member to push a dental tool out of the tool engaging member.

9. The structure of claim 1 further comprising:
   (a) the head having an opening through the end opposite the head recess for receipt of a pin; and
   (b) said tool engaging member having a rear opening aligned with the pin opening of the head; and
   (c) an extractor pin having a shaft sized to pass through said head pin opening and said tool engaging member rear opeing to push a dental tool out of the tool engaging member.

10. A dental handpiece assembly for rotating a dental tool, comprising:
    (a) a head for receiving the tool, the head having a recess at the end of the head from which the tool extends, said recess has a surface; and
    (b) the head having a bore extending into said recess, said head bore being of smaller diameter than the diameter of the recess; and
    (c) a bearing having a cylindrical bore mounted within said head bore and projecting into said head recess; and
    (d) a burr tube mounted within the bearing bore for rotation therein; and
    (e) a tool engaging member mounted to said burr tube to be rotatably driven thereby to rotate a tool engaged to said engaging member; and
    (f) a flexible skirt connected to said tool engaging member and extending rearwardly from said connection, the end of the skirt being positioned by said burr tube so that upon rotation of the skirt relative to the head the skirt is moved by centrifugal force outwardly towards the recess surface.

11. The structure of claim 10 further comprising:
    (a) a cap at the head of the handpiece opposite said head recess;
    (b) a driven gear drivingly engaged to the burr tube and aligned with the burr tube;
    (c) said cap, driven gear, burr tube and tool engaging members each having aligned bores for passage of an extractor pin; and
    (d) an extractor pin having a shaft sized to pass through the bores of the cap, driven gear, burr tube and tool engaging member to push a dental tool out of the tool engaging member.

* * * * *